(12) United States Patent
Chen et al.

(10) Patent No.: US 6,686,499 B1
(45) Date of Patent: Feb. 3, 2004

(54) METHOD FOR MAKING 2-(N-PHENYLAMINO)BENZOIC ACIDS

(75) Inventors: Michael Huai Gu Chen, Ann Arbor, MI (US); Javier Magano, Ypsilanti, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/913,872

(22) PCT Filed: Feb. 16, 2000

(86) PCT No.: PCT/US00/03982

§ 371 (c)(1),
(2), (4) Date: Aug. 20, 2001

(87) PCT Pub. No.: WO00/64856

PCT Pub. Date: Nov. 2, 2000

Related U.S. Application Data

(60) Provisional application No. 60/130,384, filed on Apr. 21, 1999.

(51) Int. Cl.[7] ............................................. C07C 229/00
(52) U.S. Cl. ..................................... 562/456; 562/457
(58) Field of Search .................................. 562/456, 457

(56) References Cited

U.S. PATENT DOCUMENTS

| | | | |
|---|---|---|---|
| 5,166,441 A | * | 11/1992 | Moldt |
| 5,612,483 A |   | 3/1997 | Jautelat |

FOREIGN PATENT DOCUMENTS

| | | |
|---|---|---|
| WO | WO 98/37881 A1 | 9/1998 |
| WO | WO 98/37881 A1 * | 9/1998 |
| WO | WO 99/01426 A1 | 1/1999 |

OTHER PUBLICATIONS

International Search Report PCT/US00/03982, May 2001.

* cited by examiner

*Primary Examiner*—Johann Richter
*Assistant Examiner*—Paul A. Zucker
(74) *Attorney, Agent, or Firm*—Charles W. Ashbrook; Steven R. Eck

(57) ABSTRACT

The present invention relates to a method for making 2-N-phenylamino)benzoic acids by coupling a benzoic acid and an aniline using an alkaline metal hexamethyldisilazide as a base.

10 Claims, No Drawings

METHOD FOR MAKING 2-(N-PHENYLAMINO)BENZOIC ACIDS

This application is a 371 of PCT/US00/038982 filed Feb. 16, 2000 which claims benefit of provisional application No. 60/130,384 filed Apr. 21, 1999.

FIELD OF THE INVENTION

The present invention relates to a method for making 2-(N-phenylamino)benzoic acids by coupling a benzoic acid and an aniline.

BACKGROUND OF THE INVENTION

The compound 2-(2-chloro-4-iodo-phenylamino)-N-cyclopropylmethoxy-3,4-difluoro-benzamine is being developed as a selective MEK-1 inhibitor for the treatment of proliferative diseases, including cancer, restenosis, psoriasis, and atherosclerosis. See, for example, U.S. Patent Application No. 60/051,440, filed Jul. 1, 1997, or PCT Published patent Application Number WO 99/01426, published Jan. 14, 1999, which are hereby incorporated by reference. To make 2-(2-chloro-4-iodo-phenylamino)-N-cyclopropylmethoxy-3,4-difluoro-benzamine, one of the intermediates that is needed is a 2-(N-phenylamino)benzoic acid. The present invention provides a method for making 2-(N-phenylamino)benzoic acids.

SUMMARY OF THE INVENTION

The present invention provides a method for making 2-(N-phenylamino)benzoic acids, the method comprising the step of reacting a benzoic acid having the Formula I

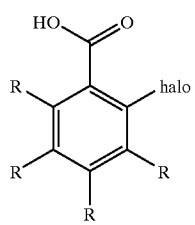

and an aniline having the Formula II

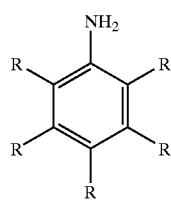

with an alkaline metal hexamethyldisilazide to form a 2-(N-phenylamino)benzoic acid having the Formula III

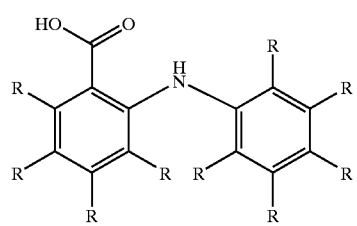

wherein
each R is independently hydrogen, halogen, $C_1-C_6$ alkyl, $-OC_1-C_6$ alkyl, CN, or $NO_2$.

In a preferred embodiment of the invention, the alkaline metal hexamethyldisilazide is lithium hexamethyldisilazide (LiHMDS).

In another preferred embodiment of the invention, the alkaline metal hexamethyldisilazide is about 3 equivalents or more with respect to the benzoic acid.

In another preferred embodiment of the invention, the halo substituent in the 2 position of the benzoic acid is fluorine.

In another preferred embodiment of the invention, the reaction is carried out at about −78° C. to about 25° C. in a polar, aprotic solvent.

In a more preferred embodiment, the solvent is tetrahydrofuran.

In another preferred embodiment of the invention, the benzoic acid is 2,3,4,-trifluorobenzoic acid and the aniline is 2-chloro-4-iodoaniline.

In another preferred embodiment of the invention, the benzoic acid and the aniline are present in about a 1:1 molar ratio.

In another preferred embodiment of the invention, one or more of the substituents R on the aniline is an electron donating group.

In another preferred embodiment of the invention, the electron donating group on the aniline is $-OCH_3$.

DETAILED DESCRIPTION OF THE INVENTION

The present invention provides a method for making 2-(N-phenylamino)benzoic acids. The method comprises the coupling of a benzoic acid having the Formula I

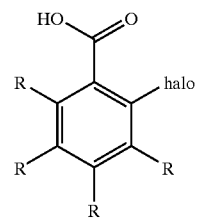

and an aniline having the Formula II

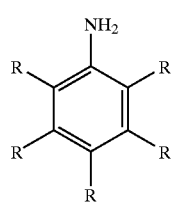

using an alkaline metal hexamethyldisilazide as a base to form a 2-(N-phenylamino)benzoic acid having the Formula III

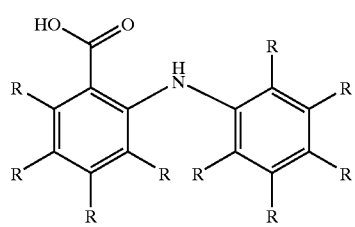

This coupling reaction preferably uses about 1 equivalent each of the benzoic acid and the aniline. Thus, the molar ratio of the benzoic acid to the aniline is about 1:1. In addition, about 3 equivalents of the alkaline metal hexamethyldisilazide is preferred; however, it is possible to use more than 3 equivalents of the alkaline metal hexamethyldisilazide. In other words, about 3 moles of alkaline metal hexamethyldisilazide to every 1 mole of benzoic acid or aniline is typically used. Lithium hexamethyldisilazide is also known as lithium bis(trimethylsilyl)amide, which can be purchased from Aldrich, Milwaukee, Wis.

The selection of an alkaline metal hexamethyldisilazide as a base is important because this base provides for an unexpected and surprising increase in the yield of the resulting 2-(N-phenylamino)benzoic acid when compared with other bases that are not alkaline metal hexamethyldisilazides. A most preferred alkaline metal hexamethyldisilazide is lithium hexamethyldisilazide.

The coupling reaction of the benzoic acid and the aniline can be carried out in a single pot process or in a multiple pot process. Other methods and sequences for carrying out the coupling reaction can be easily determined by those skilled in the art. Three procedures are specifically illustrated below.

The first procedure, called Method A, is a two-pot procedure. In a first flask, LiHMDS (1 equivalent) was added to a solution of the benzoic acid (1 equivalent) in tetrahydrofuran (THF) at −78° C. In a second flask, LiHMDS (2 equivalents) was added to a solution of the aniline (1 equivalent) in THF at −78° C. The contents from the first flask were transferred into the second flask and the resulting mixture allowed to reach ambient temperature overnight. The product was then purified by flash column chromatography.

The second method, called Method B, is a one-pot procedure. Both the benzoic acid (1 equivalent) and the aniline (1 equivalent) were dissolved in THF. The solution was cooled to −78° C. and the LiHMDS added, and the mixture was allowed to warm up to ambient temperature overnight. The product was then purified by flash column chromatography.

The third method, called Method C, is a two-pot procedure. Method C is similar to Method A, except that the 3 equivalents of LiHMDS are added to the aniline followed by a solution of the benzoic acid in THF.

The results of the coupling of various benzoic acids with various anilines is shown in Table 1 below.

TABLE 1

| Benzoic Acid | Aniline | Base | Method | Isolated Yield % | Melting point, ° C. |
|---|---|---|---|---|---|
| COOH, F, F, F, Br (tetrasubstituted) | NH₂, Cl, I | LiHMDS | A | 89 | >250 |
|  |  | LiHMDS | B | 70 | 250 |
| COOH, F, F, F | NH₂, CH₃, I | LiHMDS | A | 84 | 234–235 |
|  |  |  | B | 78 | 233–234 |
| COOH, F | NH₂, OCH₃ (H₃CO para) | LiHMDS | A | 71 | 170–172 |
| COOH, F | NH₂, OCH₃ | LiHMDS | A | 47 |  |
| COOH, F, O₂N | NH₂, F | LiHMDS | A | 94 | 234–235 |
|  |  | LiHMDS | B | 58 | 235–236 |

TABLE 1-continued

| Benzoic Acid | Aniline | Base | Method | Isolated Yield % | Melting point, °C. |
|---|---|---|---|---|---|
| COOH, F, F, F (2,3,4-trifluorobenzoic acid) | NH₂, Cl, I (4-iodo-2-chloroaniline) | LiHMDS | A | 87 | 228–229 |

Alkali metal hexamethyldisilazide bases gives unexpectedly superior yields of the 2-(N-phenylamino)benzoic acid when compared with other bases that are not alkali metal hexamethyldisilazides. For example, in the reaction between 2,3,4-trifluorobenzoic acid and 4-iodo-2-methylaniline, the yields were 84% using LiHMDS and only 28% using lithium diisopropylamine (LDA). Moreover, no reaction was observed using NaH or triethylamine (TEA). The results of these comparisons are shown in Table 2 below.

TABLE 2

| Benzoic Acid | Aniline | Method | Base | % Yield |
|---|---|---|---|---|
| COOH, F, F, F | NH₂, CH₃, I | A | LiHMDS | 84 |
| | | A | NaHMDS | 49 |
| | | A | KHMDS | 77 |
| | | B | LDA | 29 |
| | | B | NaH | 0 |
| | | B | TEA | 0 |

In addition, the amount of base used is important. Reducing the number of equivalents from 3 to 2 decreases the yield of the 2-(N-phenylamino)benzoic acid. The results are shown in Table 3. The use of more than 3 equivalents of base did not have a significant effect on the yield.

TABLE 3

| Fluorinated Compound | Aniline | Method | Base | Equivalents of Base | % Yield |
|---|---|---|---|---|---|
| COOH, F, F, F | NH₂, CH₃, I | A | LiHMDS | 2 | 26 |
| | | A | LiHMDS | 3 | 84 |
| | | A | LiHMDS | 3.5 | 88 |
| | | A | LiHMDS | 4 | 85 |

TABLE 4

| Fluorinated Compound | Aniline | Method | Base | Yield |
|---|---|---|---|---|
| COOH, F (2-fluorobenzoic acid) | NH₂, H₃CO (p-anisidine) | A | LiHMDS | 71 |
| COOH, F (4-fluorobenzoic acid) | NH₂, H₃CO | A | LiHMDS | 0 |

Thus, the reaction between 2-fluorobenzoic acid and p-anisidine afforded 71% of the desired product. In contrast, when 4-fluorobenzoic acid was employed, no reaction was observed.

The substituents on the aniline ring also affect the yield of the resulting 2-(N-phenylamino)benzoic acid. For example, the presence of electron-donating groups, such as —OC$_1$–C$_6$ The position of the halogen atom with respect to the carboxylic acid group on the benzoic acid is also important. For example, only 2-fluorobenzoic acids reacts with anilines to give the appropriate 2-(N-phenylamino)benzoic acid. Table 4 shows the results of variation of the position of the halogen atom with respect to the carboxylic acid group on the benzoic acid.

alkyl, halogen, C$_1$–C$_6$ alkyl, dialkylanimes, or —SC$_1$–C$_6$ alkyl, and others well-known to those skilled in the art, increases the reactivity of the aniline and results in a higher yield of the 2-(N-phenylamino)benzoic acid. If electron-withdrawing groups such as nitro, halogen, carbonyl (both aldehyde and ketone), ester and nitrile, and others well-known to those skilled in the art, are substituents on the aniline, the reactivity decreases and the yield of the 2-(N-phenylamino)benzoic acid is reduced. These findings are summarized in Table 6.

TABLE 6

| Fluorinated Compound | Aniline | Entry No. | Method | Base | Yield |
|---|---|---|---|---|---|
| COOH, F | NH₂, H₃CO | 1 | A | LiHMDS | 71 |
| COOH, F | NH₂, O₂N | 2 | A | LiHMDS | 0 |

In addition, the presence of electron withdrawing groups on the benzoic acid can enhance the reactivity of the benzoic acid with the aniline, and therefore, increase the yield of the resulting 2-(N-phenylamino)benzoic acid.

The reaction is typically run in a solvent. The most preferred solvents are polar, aprotic solvents such as tetrahydrofuran and diethyl ether. The temperature of the reaction is selected to provide for the greatest yield. A suitable temperature can be easily selected by one skilled in the art. A preferred temperature range is about −78° C. to about 25° C.

The examples presented herein are intended to be illustrative of the invention and are not intended to limit the scope of the specification or the claims in any manner.

What is claimed is:

1. A method for making 2-(N-phenylamino)benzoic acids, the method comprising the step of reacting a benzoic acid having the Formula I

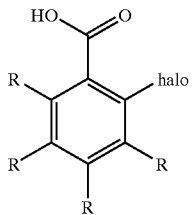

and an aniline having the Formula II

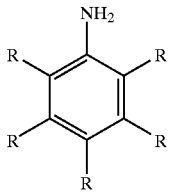

with an alkaline metal hexamethyldisilazide to form a 2-(N-phenylamino)benzoic acid having the Formula III

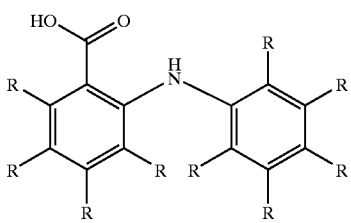

wherein each R is independently hydrogen, halogen, $C_1$–$C_6$alkyl, —$OC_1$–$C_6$ alkyl, CN, or $NO_2$.

2. The method of claim 1 wherein the alkaline metal hexamethyldisilazide is lithium hexamethyldisilazide.

3. The method of claim 1 wherein the alkaline metal hexamethyldisilazide is about 3 equivalents or more with respect to the benzoic acid.

4. The method of claim 1 wherein the halo substituent in the 2 position of the benzoic acid is fluorine.

5. The method of claim 1 wherein the reaction is carried out at about −78° C. to about 25° C. in a polar aprotic solvent.

6. The method of claim 5 wherein the polar aprotic solvent is tetrahydrofuran.

7. The method of claim 1 wherein the benzoic acid is 2,3,4,-trifluorobenzoic acid and the aniline is 2-chloro-4-iodoaniline.

8. The method of claim 1 wherein the benzoic acid and the aniline are present in about a 1:1 molar ratio.

9. The method of claim 1 wherein one or more of the substituents, R, on the aniline is an electron donating group.

10. The method of claim 9 wherein the electron donating group is —$OCH_3$.

* * * * *